(12) United States Patent
Kleiner et al.

(10) Patent No.: US 8,828,069 B2
(45) Date of Patent: Sep. 9, 2014

(54) COATING CONSTRUCT CONTAINING POLY(VINYL ALCOHOL)

(75) Inventors: Lothar W. Kleiner, Los Altos, CA (US); Jessica Reneé DesNoyer, San Jose, CA (US); Thierry Glauser, Redwood City, CA (US); Stephen D. Pacetti, San Jose, CA (US); Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 935 days.

(21) Appl. No.: 12/546,534

(22) Filed: Aug. 24, 2009

(65) Prior Publication Data

US 2009/0311301 A1    Dec. 17, 2009

Related U.S. Application Data

(62) Division of application No. 11/365,392, filed on Feb. 28, 2006, now Pat. No. 7,601,383.

(51) Int. Cl.
*A61F 2/06* (2013.01)
*A61L 31/16* (2006.01)
*A61L 31/10* (2006.01)

(52) U.S. Cl.
CPC ........... *A61L 31/16* (2013.01); *A61L 2300/422* (2013.01); *A61L 2300/606* (2013.01); *A61L 31/10* (2013.01); *A61L 2300/416* (2013.01)
USPC .............. 623/1.1; 528/310; 525/60; 424/423; 427/2.3; 427/2.24; 427/2.25; 427/2.28; 427/230

(58) Field of Classification Search
USPC ...................... 526/242; 427/2.3, 2.28; 525/60; 424/423, 145.1, 9.2; 528/310; 623/1.1; 435/70.21
See application file for complete search history.

(56) References Cited

U.S. PATENT DOCUMENTS

| | | | |
|---|---|---|---|
| 5,914,182 A * | 6/1999 | Drumheller | 428/308.4 |
| 6,287,628 B1 | 9/2001 | Hossainy et al. | |
| 2001/0014717 A1 | 8/2001 | Hossainy et al. | |
| 2003/0088307 A1 | 5/2003 | Shulze et al. | |
| 2003/0108588 A1 | 6/2003 | Chen et al. | |
| 2004/0086542 A1 | 5/2004 | Hossainy et al. | |
| 2004/0224001 A1 | 11/2004 | Pacetti et al. | |
| 2005/0070936 A1 | 3/2005 | Pacetti | |
| 2005/0143808 A1 | 6/2005 | Hossainy et al. | |
| 2005/0187376 A1 | 8/2005 | Pacetti | |
| 2005/0271663 A1 * | 12/2005 | Ignatovich et al. | 424/145.1 |
| 2005/0287184 A1 | 12/2005 | Hossainy et al. | |
| 2005/0288481 A1 | 12/2005 | DesNoyer et al. | |
| 2007/0142905 A1 * | 6/2007 | Hezi-Yamit et al. | 623/1.42 |

FOREIGN PATENT DOCUMENTS

| | | |
|---|---|---|
| JP | 2002 345972 | 12/2002 |
| WO | WO 2005/004945 | 1/2005 |

OTHER PUBLICATIONS

Serajuddin et al., Salt Formation to Improve Drug Solubility, 2007, Advanced Drug Delivery Reviews, 59, pp. 603-616.*
International Search Report for PCT/US2007/002418, filed Jan. 29, 2007, mailed Jul. 10, 2007, 15 pgs.

* cited by examiner

*Primary Examiner* — Dah-Wei D Yuan
*Assistant Examiner* — Andrew Bowman
(74) *Attorney, Agent, or Firm* — Squire Patton Boggs (US) LLP

(57) ABSTRACT

A method of forming a surface layer that includes a hydroxyl polymer on a substrate coating on a medical device is provided.

29 Claims, No Drawings

COATING CONSTRUCT CONTAINING POLY(VINYL ALCOHOL)

CROSS-REFERENCE TO RELATED APPLICATIONS

This is a divisional application of U.S. application Ser. No. 11/365,392, filed on Feb. 28, 2006, now U.S. Pat. No. 7,601,383, the teaching of which is incorporated herein in its entirety by reference.

FIELD OF THE INVENTION

This invention is generally related to forming a hydrophilic layer of coating for implantable medical devices, such as drug delivery vascular stents.

DESCRIPTION OF THE STATE OF THE ART

Stents are used not only as a mechanical intervention of vascular conditions but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents that have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents, e.g., stents with a coating that includes an agent, provide for the local administration of a therapeutic substance at the diseased site. In order to provide an effective concentration at the treated site, systemic administration of useful medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

Coatings on a medical device such as a stent are often desired to have a surface that can be modified to meet different biological or therapeutic needs. Coatings formed of inert hydrophobic materials can have a surface that is hard to modify. One strategy is to incorporate hydrophilic moieties into the coating. To incorporate hydrophilic moieties, the hydrophobic surface must be modified to make it compatible with those moieties or hydrophilic layers in a coating. Otherwise, the hydrophilic moieties or layers of coating will either "wash off" or render a coating with poor mechanical integrity.

The embodiments described below address the above-identified problem.

SUMMARY

Provided herein is a method for modifying a hydrophobic surface of a coating by forming a hydrophilic surface layer on the hydrophobic surface. The method includes contacting a substrate coating with a solution that includes a hydroxyl polymer (e.g. poly(vinyl alcohol) (PVOH) or a copolymer thereof) and a solvent to allow the hydroxyl polymer to adsorb onto, into, or both onto and into the substrate coating surface, removing the coating from the solution, and drying the coating to form an adhesion layer that includes the hydroxyl polymer.

In some embodiments, the hydroxyl polymer can have a general formula as shown below:

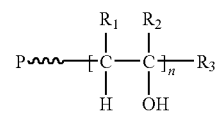

where:

P can be H, $CH_3$, absence, ethylene vinyl alcohol, or a polymeric, oligomeric or monomeric unit(s). For example, P can be a biocompatible polymer such as polyolefin (e.g., polyethylene), poly(ethylene glycol) (PEG), poly(propylene oxide) (PPO), poly(vinylidene fluoride) (PVDF), poly(vinyl pyrrolidone) (PVP), poly((2-hydroxyl)ethyl methacrylate) (HEMA), poly(methyl methacrylate) (MMA), hyaluronic acid (HA), benzylated HA, or other biocompatible polymers;

$R_1$ and $R_2$ are independently H, $CH_3$ and $CH_3CH_2$;

$R_3$ can be H, $CH_3$, $CH_3CH_2$, and P; and n is an integer ranging from 1 to about 1,000,000.

The layer comprising a hydroxyl polymer imparts hydrophilicity to the substrate coating. Hydrophilic surface layers can have different thicknesses. In some embodiments, the hydrophilic surface layer can have a thickness ranging from about 20 angstroms to about 5 microns.

In some embodiments, the layer of hydroxyl polymer can optionally include a bioactive agent. For example, the layer of hydroxyl polymer can be modified to conjugate with a bioactive agent to render the layer of hydroxyl polymer pro-healing or thrombo-resistant. In some other embodiments, two or more layers of hydroxyl polymers can be formed on a substrate coating, each of which can optionally include a bioactive agent, that can be the same or different. Some exemplary agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, or a combination thereof.

A medical device having the features described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, and combinations thereof.

DETAILED DESCRIPTION

Provided herein is a method for modifying a hydrophobic surface of a coating by forming a hydrophilic surface layer on the hydrophobic surface. The method includes contacting a substrate coating with a solution that includes a hydroxyl polymer (e.g. poly(vinyl alcohol) (PVOH) or a copolymer thereof) and a solvent to allow the hydroxyl polymer to adsorb onto, into, or both onto and into the substrate coating surface, removing the coating from the solution, and drying the coating to form an adhesion layer that includes the hydroxyl polymer.

The hydrophilic surface layers formed according to the methods described herein can have different thicknesses. In some embodiments, the hydrophilic layer can have a thickness ranging from about 20 angstroms to about 5 microns.

Coating Construct

A hydroxyl polymer in a solution can adsorb irreversibly onto hydrophobic surfaces, rendering them hydrophilic. The extent of polymer adsorption and thus hydrophilicity of the modified surface or coating can depend upon solution concentration, contact time, and the nature of the hydrophobic surface. Films that are adsorbed from dilute solutions of the hydroxyl polymer tend to be thinner and more crystalline while films that are adsorbed from more concentrated solutions tend to contain more loosely packed hydroxyl polymer chains that are less hydrogen bound to one another and thus more available to interact with surrounding aqueous media. This ability to tailor the hydrophilicity of a hydroxyl polymer surface enables a variety of surface modification chemistries. Additionally, the hydroxyl polymer is amenable to forming multiple polymer layers. For example, a medical device having a surface of hydrophobic polymer can be placed in a solution of a hydroxyl polymer to allow the hydroxyl polymer to adsorb onto the surface into a layer. The device can then be removed from the solution, dried, and replaced in the solution to allow the formation of another layer of the hydroxyl polymer. Following this route, multiple layers of hydroxyl polymer can be built up on the surface. Moreover, varying the solution concentration or contact time, can form multiple layers of hydroxyl polymers with different properties.

Accordingly, in some embodiments, a medical device (e.g. stent) can be made to have a coating that includes a layer of a hydroxyl polymer coated from a solution of a hydroxyl polymer. In some embodiments, the solution of the hydroxyl polymer can be a dilute solution. The dilute solution can have a concentration of the hydroxyl polymer ranging from e.g., about 20 to about 0.01 mol %. In some embodiments, the dilute solution can have a concentration of the hydroxyl polymer about 0.01 mol % or less.

In yet other embodiments, a medical device (e.g. stent) can have a coating that includes a layer of a hydroxyl polymer coated from a more concentrated solution of the hydroxyl polymer. The more concentrated solution can have a concentration of the hydroxyl polymer ranging from about 20 mol % to about 1 mol %.

In some embodiments, a medical device (e.g. stent) can have a coating that includes two or more layers of the hydroxyl polymer, one layer coated from a dilute solution of the hydroxyl polymer, the other coated from a concentrated solution of the hydroxyl polymer. The dilute solution of hydroxyl polymer can have a concentration ranging from e.g., about 20 to about 0.01 mol %. In some embodiments, the dilute solution can have a concentration of the hydroxyl polymer about 0.01 mol % or less. The more concentrated solution can have a concentration of the hydroxyl polymer ranging from about 20 mol % to about 1 mol %.

In some further embodiments, a medical device (e.g. stent) can have a coating that includes two or more layers of hydroxyl polymers, one layer coated from a hydroxyl polymer solution in one solvent, the other coated from a hydroxyl polymer solution in a different solvent. Different solvents can have different chemical and physical properties (e.g. different boiling points and/or polarity) so as to impart different properties to the layer of hydroxyl polymer.

In some further embodiments, a layer of hydroxyl polymer in a coating on a medical device (e.g., stent) can include one or more agents. Where the coating includes two or more layers of hydroxyl polymer, each of the layers of hydroxyl polymer can have an agent that can be the same or different. The different agents can impart different biological and/or medicinal properties to the coating. For example, a layer with a prohealing moiety coupled to the hydroxyl polymer can underlie another layer of hydroxyl polymer used to facilitate a thrombo-resistant surface.

In some embodiments, the hydroxyl polymer can be any polymer derived from vinyl alcohol, having a general formula as shown below:

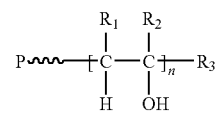

where:

P can be H, $CH_3$, absence, ethylene vinyl alcohol, or a polymeric, oligomeric or monomeric unit(s). For example, P can be a biocompatible polymer such as polyolefin (e.g., polyethylene), poly(ethylene glycol) (PEG), poly(propylene oxide) (PPO), poly(vinylidene fluoride) (PVDF), poly(vinyl pyrrolidone) (PVP), poly((2-hydroxyl)ethyl methacrylate) (HEMA), poly(methyl methacrylate) (MMA), hyaluronic acid (HA), benzylated HA, or other biocompatible polymers;

$R_1$ and $R_2$ are independently H, $CH_3$ and $CH_3CH_2$;

$R_3$ can be H, $CH_3$, $CH_3CH_2$, and P; and n is an integer ranging from 1 to about 1,000,000.

The hydroxyl polymer can have different content of the repeating units derived from the vinyl alcohol monomer, ranging from about 100 mole % to about 1.00 mole %, e.g., about 95 mole %, about 90 mole %, about 85 mole %, about 80 mole %, about 75 mole %, about 70 mole %, about 65 mole %, about 60 mole %, about 55 mole %, about 50 mole %, about 45 mole %, about 40 mole %, about 35 mole %, about 30 mole %, about 25 mole %, about 20 mole %, about 15 mole %, about 10 mole %, or about 5 mole %. In one embodiment, the hydroxyl polymer is poly(ethylene-co-vinyl alcohol) (EVAL) having about 27 mole % ethylenyl units. In another embodiment, the hydroxyl polymer is PVOH.

Coating Solvents for Hydroxyl Polymers

A variety of solvents can be used to form the layer of hydroxyl polymer described herein. Generally, the solvent is capable of dissolving PVOH and, if an agent is included in the PVOH, the agent. In some embodiments, where the layer of hydroxyl polymer is formed on top of a drug reservoir layer, the coating solvent for the layer of hydroxyl polymer preferably does not dissolve, or has a low solubility for the drug (e.g., everolimus) in the drug reservoir.

Some representative coating solvents for coating the layer of hydroxyl polymer include, but are not limited to, water, dimethyl sulfoxide (DMSO), dimethyl acetamide (DMAC), alcohols such as methanol, ethanol, propanol, isopropanol, butanol, mixtures thereof, or a mixture thereof with water.

Method of Forming a Layer of Hydroxyl Polymer

A layer of hydroxyl polymer can be formed on a coating on a medical device (e.g., a stent) via established procedures, e.g., by dipping, soaking, spray coating, etc. The 1 hydroxyl polymer layer can have a thickness, from about 25-50 angstrom to about 100 microns. In some embodiments, the layer of hydroxyl polymer can have a thickness of about 0.1 to about 0.5 microns. Controlling the concentration of the PVOH solution and the time of adsorption can control the thickness of the hydroxyl polymer layer. For example, the equilibrium thickness of PVOH deposition onto a surface of poly(tetrafluoroethylene-co-hexafluoropropylene) (FEP) takes approximately 24 hours when the surface is exposed to a water solution of PVOH (Kozlov, M., Quarmyne, M., Chen, W. & McCarthy, T. J., Adsorption of Poly(vinyl alcohol) onto hydrophobic substrates. A general approach for hydrophilizing and chemically activating surfaces. Macromolecules 36:6054-6059 (2003). However, a measurable layer of hydroxyl polymer can be formed on the surface of a medical device in about 9 minutes or less.

In some embodiments, there is a need to keep the drug (e.g., everolimus) in the reservoir layer from being released during deposition of the hydroxyl polymer. This can be accomplished by using the following measures:

(1) saturating a soaking/coating solution of the hydroxyl polymer with the drug, (2) elevating the ionic strength of a coating solution of hydroxyl polymer so that its solubility for the drug is reduced, (3) minimizing the solution volume of a hydroxyl polymer solution such that the amount of the drug that may be released from the reservoir is also small, or (4) selecting a solvent or solvent mixture capable of dissolving the hydroxyl polymer but not the drug and the reservoir layer.

"Small" as used for describing the solution volume of a hydroxyl polymer solution refers to a volume of the solution sufficient to cover the device. In some embodiments, a small volume is less than about 1 mL; in these or other embodiments a small volume is about 750 µL.

During the drying process, the hydroxyl polymer can partially crystallize. In some embodiments, placing the layer of hydroxyl polymer in a high humidity atmosphere and annealing it can promote additional crystallization. The hydroxyl polymer layer can affect the drug release rate from the device depending on the drug properties. For everolimus, the drug release rate is not expected to be greatly affected by the hydroxyl polymer layer.

Surface Modification of Layer of Hydroxyl Polymer

In some embodiments, pendant or functional group attachment to the layer of hydroxyl polymer can modify the hydrophilic surface. For example, several strategies have been established to conjugate a chosen compound to the mildly reactive hydroxyl groups in the hydroxyl polymer.

In one embodiment, polyethylene glycol (PEG) can attach to the hydroxyl polymer. As attached, PEG can serve as a spacer between the hydroxyl polymer surface and an agent such as a peptide, protein, or a drug molecule. To serve as a spacer, one end of PEG can be, e.g., an amine group protected with a protective group such as methoxycarbonyl (MOC) or 9-fluorenylmethyoxycarbonyl (FMOC), while the other end of PEG can be any of the following groups:

(a) a carboxylic acid or N-hydroxysuccinimide (NHS)—coupling of the PEG to the hydroxyl polymer surface can be readily accomplished in the presence of N,N'-carbonyldiimidazole or dicyclohexylcarbodiimide (DCC), which are commercially available;

(b) an acid chloride—PEG can be easily functionalized using acryloyl chloride; and (c) a vinyl sulphone—coupling of PEG to the surface of the hydroxyl polymer can be achieved under acidic conditions.

Upon completion of attaching the PEG to the surface of the hydroxyl polymer, the protecting group on the PEG molecule can be removed, yielding a hydroxyl polymer surface with dangling, amine-terminated, PEG chains. The amine group can be used to conjugate with a bioactive agent such as a pro-healing agent. Alternatively, the protected end of PEG can be an aldehyde or a protected carboxylic acid group. Upon attaching the other end of PEG to the hydroxyl polymer surface, the protective groups can be removed, yielding a hydroxyl polymer surface with dangling, aldehyde- or carboxylic-acid-terminated PEG chains. The aldehyde or carboxylic acid groups then can conjugate with an agent such as a drug molecule.

Chemistries of attaching different spacers to a surface of the hydroxyl polymer are well documented in the art. Chemistries for conjugating the spacer to an agent such as a peptide or a drug molecule are well documented in the art, as well. (see, e.g., Cabral, J. M. S; Kennedy, J. F. In Protein Immobilization, Fundamental and Applications; Taylor, R. F., Ed; Marcel Dekker, Inc.: New York, 1991; Chapter 3, pp 74).

In some embodiments, the surface of the hydroxyl polymer can be made more stable by including in the surface layer a material capable of minimizing the interfacial energy between the layer of hydroxyl polymer and the hydrophobic coating or layer underneath. Such a material generally has a hydrophobic section and a hydrophilic section in the molecule. Examples of such materials include, but are not limited to, poly(propylene oxide-co-vinyl alcohol) (PPO-co-PVOH), or poly(vinylidene fluoride-co-vinyl alcohol) (PVDF-co-PVOH). In some embodiments the material is polymeric. In some embodiments, the surface of the hydroxyl polymer can be made more stable by crosslinking with a crosslinking agent such as glutaldehyde.

In some embodiments, the hydroxyl polymer layer can be further stabilized by exposing the layer to freeze-thaw cycles after coating.

In some other embodiments, the layer of hydroxyl polymer can be stabilized by forming a partial interpenetrating network (P-IPN) or semi-interpenetrating network (S-INP) of PVOH. The P-IPN or S-IPN can be formed by applying a hydroxyl polymer in a solvent selected to swell the substrate coating (e.g., a drug delivery coating or a top coating). Hydrogen bonding between molecules of PVOH in the substrate allows the formation of P-INP or S-INP morphology, thus stabilizing the hydroxyl polymer surface layer. In one embodiment, these interpenetrating networks are formed similarly as described above except that networks are additionally curing by exposure to an e-beam, UV, or plasma to graft the hydroxyl polymer or block copolymer to the substrate coating. Curing can be accomplished with or without a curing agent such as maleic or fumaric acid.

Some exemplary PVOH block copolymers include, but are not limited to, PVOH-co-HEMA, PVOH-co-MMA-HEMA, or PVOH-HA-benzylated.

In some embodiments, the hydroxyl polymer is EVAL. EVAL is commercially available in several grades. The grade that most closely resembles the behavior of PVOH is the one with the lowest ethylene content, which is the L-Series EVAL from EVALCA (which contains 27 mole % ethylene). This polymer is soluble in organic solvents such as DMSO, DMAC, and some alcohols. However, it will not dissolve in hot water (unlike pure PVOH). Consequently, this 20-mole %-ethylene EVAL can be spray or dip coated onto a substrate coating. After drying, the ethylene component may migrate to the surface. But, in an aqueous or a very polar solvent, the L-series EVAL coating will swell, and the surface will reorient more hydroxyl groups to the surface. The L-series EVAL's equilibrium water absorption is greater than 10% (w/w), which indicates that the L-series EVAL in a coating can easily swell in an aqueous environment to reorient the OH and $CH_3$ groups.

Substrate Coating

One or multiple layers of a hydroxyl polymer can be formed on the surface of any substrate coating. The substrate coating can include one or more biocompatible polymer(s). The biocompatible polymer can be biodegradable (both bioerodable or bioabsorbable) or nondegradable. Representative biocompatible polymers include, but are not limited to, poly (ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the substrate coating described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

In some embodiments, the substrate coating can further include a biobeneficial material. The biobeneficial material can be polymeric or non-polymeric. The biobeneficial material is preferably substantially non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, the substrate coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

In some embodiment, one or multiple layers of a hydroxyl polymer can be formed on the surface of a medical device formed of a polymer (e.g., a durable or bioabsorbable stent) without a coating.

Bioactive Agents

In some embodiments, the substrate coating and/or the layer of hydroxyl polymer can include one or more bioactive agents. The bioactive agents can be any bioactive agent that is therapeutic, prophylactic, or diagnostic. These agents can have anti-proliferative or anti-inflammatory properties or can have other properties such as antineoplastic, antiplatelet, anticoagulant, anti-fibrin, antithrombonic, antimitotic, antibiotic, antiallergic, and antioxidant properties. These agents can be cystostatic agents, agents that promote the healing of the endothelium such as NO releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy) propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents that may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents that are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE and ENDOTAK, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (EL-GILOY), stainless steel (316 L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A medical device having a layer formed according to a method comprising:
   providing a composition comprising a hydroxyl polymer;
   providing a medical device comprising a coating;
   forming a layer of the composition on the coating;
   attaching a spacer to the layer to generate dangling functional-group-terminated spacer chains; and
   conjugating a bioactive agent to the spacer via the functional group;
   wherein the hydroxyl polymer has a structure of

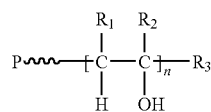

where:
   P is H, $CH_3$, absence, ethylene vinyl alcohol, or a polymeric, oligomeric or monomeric unit;
   $R_1$ and $R_2$ are independently H, $CH_3$, or $CH_3CH_2$;
   $R_3$ is H, $CH_3$, $CH_3CH_2$, or P; and
   n is an integer ranging from 1 to about 1,000,000;
   wherein the method further comprises curing the composition layer thereby grafting the hydroxyl polymer to the coating.

2. The medical device of claim 1 wherein forming comprises absorbing the hydroxyl polymer onto, into, or both the coating.

3. The medical device of claim 1 wherein P is selected from the group consisting of $CH_3$, polyolefin, poly(ethylene glycol) (PEG), polypropylene oxide) (PPO), poly(vinylidene fluoride) (PVDF), poly(vinyl pyrrolidone) (PVP), poly((2-hydroxyl)ethyl methacrylate) (HEMA), poly(methyl methacrylate) (MMA), hyaluronic acid (HA), benzylated HA, poly(ethylene-co-vinyl alcohol) (EVAL), and combinations thereof.

4. The medical device of claim 1 wherein the hydroxyl polymer is poly(vinyl alcohol) (PVOH) or EVAL.

5. The medical device of claim 1 further comprising forming an additional layer comprising the hydroxyl polymer.

6. The medical device of claim 2 wherein the composition layer has a thickness from 20 angstroms to about 5 microns.

7. The medical device of claim 5 wherein the composition layer and the additional layer independently have a thickness from 20 angstroms to about 5 microns.

8. The medical device of claim 1 wherein the coating comprises a bioactive agent.

9. The medical device of claim 8 wherein the agent is selected from the group consisting of paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and a combination thereof.

10. The medical device of claim 1, wherein the hydroxyl polymer is PVOH, and wherein the composition further comprises a block copolymer comprising PVOH.

11. The medical device of claim 1, wherein the hydroxyl polymer is PVOH, and wherein the composition layer further comprises a block copolymer comprising PVOH.

12. The medical device of claim 1 wherein the hydroxyl polymer is a block copolymer selected from the group consisting of poly(propylene oxide-co-vinyl alcohol) (PPO-co-PVOH), poly(vinylidene fluoride-co-vinyl alcohol) (PVDF-co-PVOH), EVAL, and combinations thereof.

13. The medical device of claim 1, wherein the method further comprises treating the composition layer to freeze-thaw cycle(s) to increase the stability of the layer.

14. The medical device of claim 1 wherein forming comprises:
   swelling the coating with the solution of the composition, and
   forming the composition layer on the coating,
   wherein the composition is dissolved in a solvent capable of partially swelling the coating.

15. The medical device of claim 1 wherein curing is achieved by e-beam, UV irradiation or plasma exposure.

16. The medical device of claim 15 wherein curing of the composition layer is in presence of a curing agent which is maleic acid, fumaric acid, or combination thereof.

17. The medical device of claim 8 wherein the composition layer further comprises a bioactive agent that is the same as the bioactive agent in the coating or different from the bioactive agent in the coating.

18. The medical device of claim 17 wherein the bioactive agent is paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and a combination thereof.

19. The medical device of claim 1 wherein the hydroxyl polymer is PVOH, and the method further comprises exposing the layer to a humid environment to promote additional crystallization of the PVOH.

20. The medical device of claim 1, wherein the method further comprises
   including a material capable of minimizing the interfacial energy between the layer of hydroxyl polymer and the coating beneath so to make the surface of the hydroxyl polymer more stable; wherein the material is polypropylene oxide-co-vinyl alcohol) or poly(vinylidene fluoride-co-vinyl alcohol); or
   crosslinking the hydroxyl polymer using glutaldehyde.

21. The medical device of claim 1 wherein the bioactive agent is a pro-healing agent, an antithrombogenic agent, a non-fouling agent, or combinations thereof.

22. The medical device of claim 1 wherein the hydroxyl polymer is poly(vinyl alcohol-co-(2-hydroxyl)ethyl methacrylate) (PVOH-co-HEMA), poly(vinyl alcohol-co-methyl methacrylate-co-(2-hydroxyl)ethyl methacrylate) (PVOH-co-MMA-co-HEMA), poly(vinyl alcohol-co-hyaluronic acid) (PVOH-co-HA), poly(vinyl alcohol-co-benzylated hyaluronic acid) (PVOH-co-HA-Bz), EVAL or combinations thereof.

23. The medical device of claim 1 which is a stent.

24. The medical device of claim 22 which is a stent.

25. The medical device of claim 1 which is an absorbable stent.

26. The medical device of claim 22 which is an absorbable stent.

27. The medical device of claim 1 wherein the spacer is a poly(ethylene glycol) (PEG).

28. The medical device of claim 27 wherein the dangling functional group is selected from the group consisting of amine, carboxylic acid, and aldehyde.

29. The medical device of claim 28 wherein the attaching of the PEG to the hydroxyl polymer in the layer is via a group on the other end of the PEG, wherein the group on the other end of the PEG is selected from the group consisting of carboxylic acid, N-hydroxy succinimde, acid chloride, and vinyl sulfone.

* * * * *